United States Patent
Hornabrook et al.

(10) Patent No.: US 8,436,986 B2
(45) Date of Patent: May 7, 2013

(54) APPARATUS AND METHODS FOR ASSESSMENT, EVALUATION AND GRADING OF GEMSTONES

(75) Inventors: Graham Alfred Hornabrook, Dubbo (AU); Stuart Norman Marchant, Alstonville (AU); Rodney Herbert Lummis, Tamworth (AU); Kathryn Elizabeth Primmer, Appin (AU); Peter Bruce Sutton, Dubbo (AU); Angus Nelson Hornabrook, Clagiraba (AU); Leanne Bischof, Putney (AU); Ryan Lagerstrom, Stanmore (AU); Volker Hilsenstein, St. Lucia (AU); Robert George Imrie, Gulargambone (AU)

(73) Assignee: Opal Producers Australia Limited, New South Wales (AU)

( * ) Notice: Subject to any disclaimer, the term of this patent is extended or adjusted under 35 U.S.C. 154(b) by 766 days.

(21) Appl. No.: 12/450,652

(22) PCT Filed: Apr. 2, 2008

(86) PCT No.: PCT/AU2008/000459
§ 371 (c)(1),
(2), (4) Date: Dec. 23, 2009

(87) PCT Pub. No.: WO2008/119125
PCT Pub. Date: Oct. 9, 2008

(65) Prior Publication Data
US 2010/0111354 A1    May 6, 2010

(30) Foreign Application Priority Data
Apr. 3, 2007   (AU) ................................. 2007901825

(51) Int. Cl.
*G01N 21/00*   (2006.01)

(52) U.S. Cl.
USPC ............................................... 356/30; 356/31

(58) Field of Classification Search .................. None
See application file for complete search history.

(56) References Cited

U.S. PATENT DOCUMENTS

| 4,529,305 A | 7/1985 | Welford et al. |
| 5,828,405 A * | 10/1998 | Vanier et al. .................... 348/61 |

(Continued)

FOREIGN PATENT DOCUMENTS

| WO | WO 01/61316 A1 | 8/2001 |
| WO | WO 03/062942 A2 | 7/2003 |

(Continued)

OTHER PUBLICATIONS

International Search Report for National Application No. 2007901825 dated May 16, 2007.
PCT International Search Report for PCT/AU2008/000459 dated May 20, 2008.

*Primary Examiner* — Claire X Wang
(74) *Attorney, Agent, or Firm* — Abelman, Frayne & Schwab

(57) ABSTRACT

An apparatus (10) for assessment, evaluation and grading of gemstones has a stage (11) upon which a gemstone may be supported, the stage being enclosed in a housing (15) that is impervious to light. At least one light source (14) located in the housing is adapted to project incident light onto the gemstone. There are means for rotating and tilting the stage so as to vary the orientation of the gemstone to the incident light. A digital camera (16) is located in the housing adjacent the or each light source and is adapted to take images of the gemstone based on reflection and/or refraction of the incident light. There are also information processing means for calibrating and analyzing the images, with the information processing means being programmed with an instruction set for color calibrating the images and then analyzing the color calibrated images by segmentation and histogram measurement.

6 Claims, 17 Drawing Sheets

| U.S. PATENT DOCUMENTS | | | |
|---|---|---|---|
| 6,239,867 B1 * | 5/2001 | Aggarwal | 356/30 |
| 6,508,009 B1 | 1/2003 | Tubis et al. | |
| 2005/0036132 A1 | 2/2005 | Lapa et al. | |
| 2005/0036134 A1 | 2/2005 | Wada | |
| 2005/0069858 A1 | 3/2005 | Lapa et al. | |

| FOREIGN PATENT DOCUMENTS | | |
|---|---|---|
| WO | WO 2007/023444 A2 | 3/2007 |
| WO | WO 2007/069242 A1 | 6/2007 |

* cited by examiner

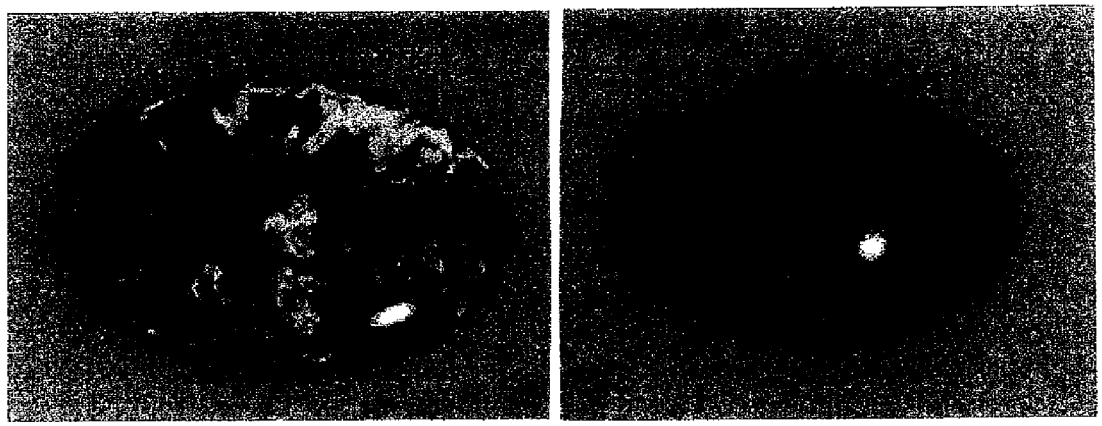
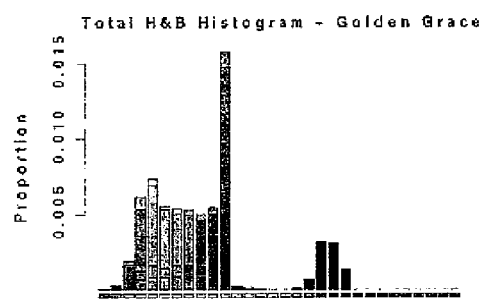
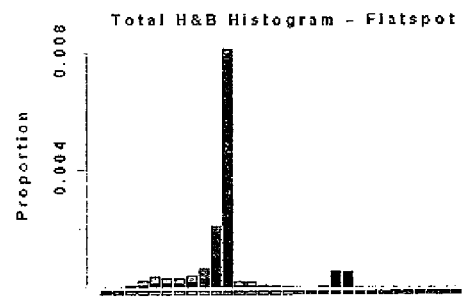
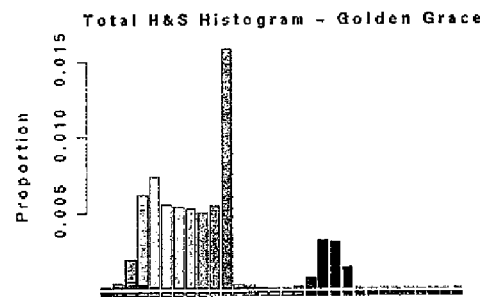
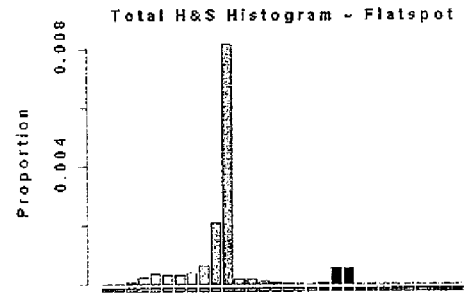
Fig. 13

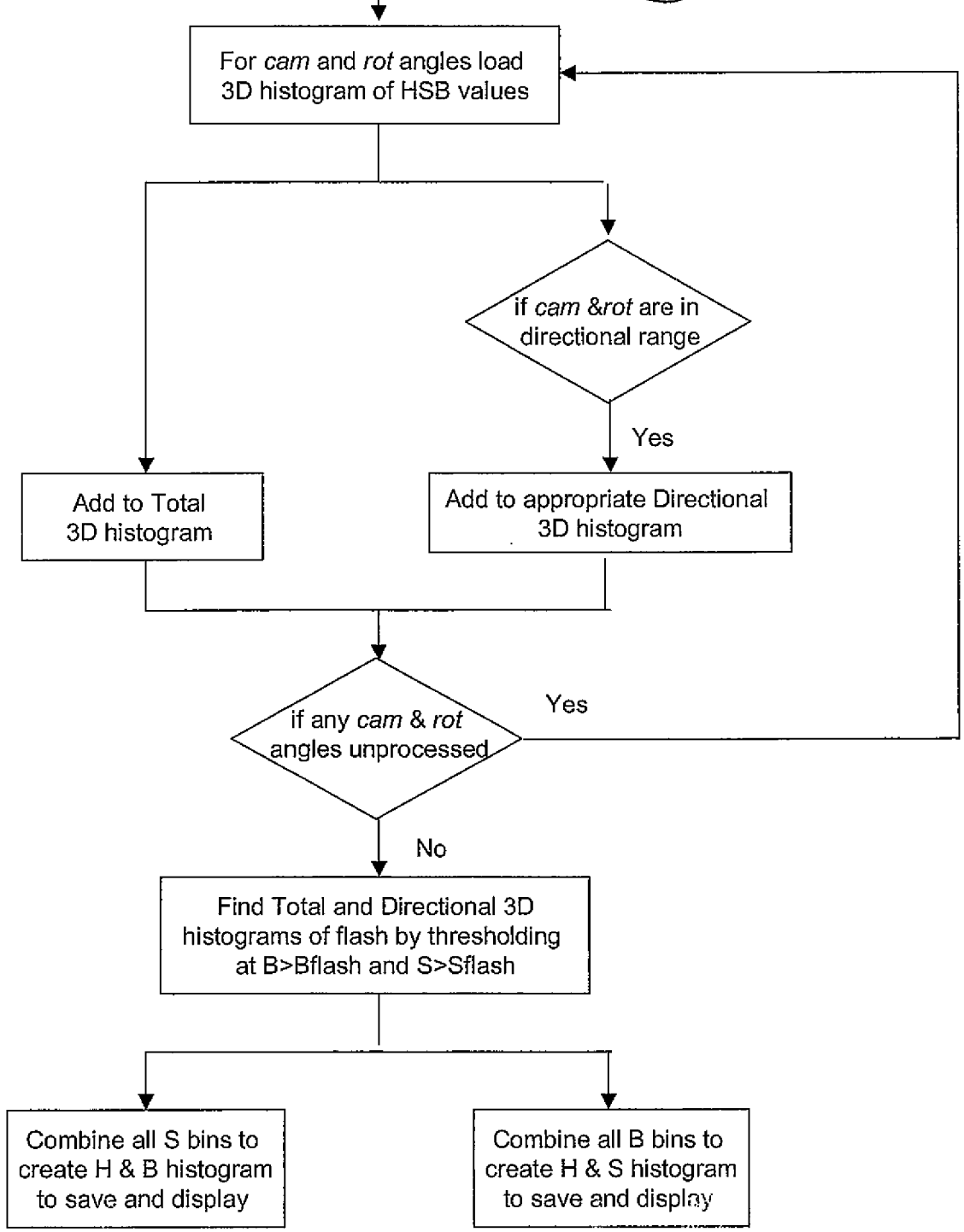

APPARATUS AND METHODS FOR ASSESSMENT, EVALUATION AND GRADING OF GEMSTONES

CROSS REFERENCE TO RELATED APPLICATIONS

This application is a national phase of PCT application No. PCT/AU2008/000459, filed Apr. 2, 2008, which claims priority to AU patent application No. 2007901825, filed Apr. 3, 2007, all of which are incorporated herein by reference.

TECHNICAL FIELD

The present invention relates to apparatus and methods for assessment, evaluation and grading of gemstones (including inorganic and organic gemstones) and minerals, such as opals, pearls and diamonds, as well as mineral specimens. In particular, the present invention relates to a digital analyser for such gemstones and minerals which incorporates both hardware and software.

Although the background of the invention and the preferred embodiments of the invention will be hereinafter described with reference to the assessment, evaluation and grading of opals, it will be apparent to persons skilled in the art that it is the intent of this specification that the invention described herein be not limited thereto, but have wider application to all gemstones and minerals. For ease of understanding in this specification, the term "gemstones(s)" will be used when referring to all gemstones and minerals that fall within the scope of the invention.

BACKGROUND ART

Current opal assessment and evaluation practices are highly subjective as they are based on a combination of human observed factors, such as scoring the flashes of colour as the opal is moved, the body tone, colour, brightness and pattern. The fact that Australia contributes 95% of the world's opals is both a blessing and a curse. Overseas buyers often do not have the training to assess the value of opals being supplied (leading to difficult negotiations between buyer and seller), nor can they describe a particular type of opal in sufficiently concise and objective terms for the suppliers to be able to provide the appropriate opals.

Most gemstone assessment is made using a magnification 10× loupe. The gemstone is observed by holding it in a pair of gemstone tweezers and turning it (using pitch, roll and yaw) to observe light interaction with the gemstone and external and internal characteristics.

The subjective nature of current opal assessment and evaluation practices creates difficulty in negotiations and substantial distortions in the terms of trade between the opal miners and the buyers.

There exist a number of key characteristics on which an opal can be graded for its value, such as:—
  Colour (hue) and area of flash
  Brightness
  Body tone
  Pattern
  Shape
  Other characteristics In terms of relative importance to the overall gemmological value of an opal, colour and body tone combined have about a 40% weighting, followed by brightness and pattern, each at about 30%, with the remaining characteristics being of much less significant weighting. In terms of seeking an objective assessment by a human observer, colour appears to be the most difficult, followed by brightness, which seems easier to assess and quantify manually, as is the pattern, of which there are 28 main types.

Colour is difficult for a human observer to assess because of the following:
  (1) The contribution of each colour changes with viewing angle, that is, with pitch, roll and yaw. All orientations are to be integrated in a colour estimation, which is difficult due to the limited perception and subjective memory of humans and their eyesight variables.
  (2) Out in the field, it is difficult to accurately assign a shade according to a colour reference chart because the conditions for viewing are highly variable.

To compound the problem, synthetic or man-made replicas of opals and other gemstones are improving, and in some cases (eg diamonds), it is extremely difficult to detect the natural gemstone from the synthetic. Verifying the authenticity of the gemstones is another problem that may be resolved by adoption of objective and automated analytical methods.

One approach to provide an objective and automated analytical method and image capture device for the grading of diamonds is disclosed in U.S. Pat. No. 6,239,867 ("the Patent"). Although also referring to use of the method and device for the grading of opals and other gemstones, that approach is unsuited to opals and is poorly suited to other gemstones, even diamonds. The image capture device and method disclosed in the Patent do not allow for gemstone movements of pitch, roll and yaw during the capture of images so as to display the "play of colours" of the gemstone, as the gemstone stage is not tiltable. Nor does the Patent disclose the assessment of all segments of the face of a gemstone for each of colour, brightness, body tone and other characteristics, many of which are especially important for opals, before grading the gemstone for each characteristic. Rather, the Patent discloses a method of sampling a small area of a diamond by moving a camera through a controlled arc and averaging the total illumination data in that area to assess the colour of the diamond.

Such a limited sampling is not suited to opals as it will not display the "play of colours", body tone and brightness of an opal over all segments. In particular, the Patent states that gemstone colour analysis is done by obtaining average red, green and blue (RGB) values for colour images in the image pixel region delineated by the girdle and the table facets, and that by sampling the colour of a smaller region a more predictable and accurate colour reading is obtained. These procedures are not suited to the assessment of opals, where it is the entire face of the opal that requires colour assessment.

Furthermore, the image capture device disclosed in the Patent filters the light between the gemstone and its camera, and this is stated to be critical to the analysis of colours. That device also uses high viscosity immersion oil either between the gemstone and a glass plate upon which it is centrally placed or to immerse the gemstone so as to remove glint and assist in the transmission of light though the gemstone for the detection of flaws or colour inclusions. These features of the image capture device and method disclosed in the Patent are unsuited to opals and are poorly suited to other gemstones.

DISCLOSURE OF INVENTION

It is an object of the present invention to overcome or substantially ameliorate the aforementioned shortcomings and problems of the prior art, or to at least provide a useful alternative.

It is another object of the present invention to provide apparatus and methods for assessment, evaluation and grading of gemstones in an objective and automated manner so as to allow standardisation of opal and other gemstone quality analysis and grades, thereby improving the confidence to trade of the sellers and also the buyers and adding certainty to the prices they may be prepared to accept or pay for a gemstone.

According to the invention, there is provided an apparatus for assessment, evaluation and grading of gemstones, comprising a stage upon which a gemstone may be supported, the stage being enclosed in a housing that is impervious to light, at least one light source located in the housing and adapted to project incident light onto the gemstone, means for rotating and tilting the stage so as to vary the orientation of the gemstone to the incident light, a digital camera located in the housing adjacent the or each light source and adapted to take images of the gemstone based on reflection and/or refraction of the incident light, and information processing means for calibrating and analysing the images, wherein the information processing means is programmed with an instruction set for colour calibrating the images and then analysing the colour calibrated images by segmentation and histogram measurement.

It is preferred that the stage is rotatable around 360° and tiltable around 90°, and may be part of a goniometer.

It is important that the camera and the or each light source be positioned as close as possible together so as to mimic human opal grading, wherein the or each light source is as near co-incident as possible to the camera axis.

BRIEF DESCRIPTION OF THE DRAWINGS

FIG. 13 provides a comparison of Summary Hue and Brightness Histograms of two different opals, and a comparison of Summary Hue and Saturation Histograms of those two opals, for images taken of the opals at an 80° tilt angle.

FIG. 15b is a continuation of the logical flow diagram of FIG. 15a.

FIG. 15c is a further continuation of the logical flow diagrams of FIG. 15a and FIG. 15b.

MODES FOR CARRYING OUT THE INVENTION

Figure 1:
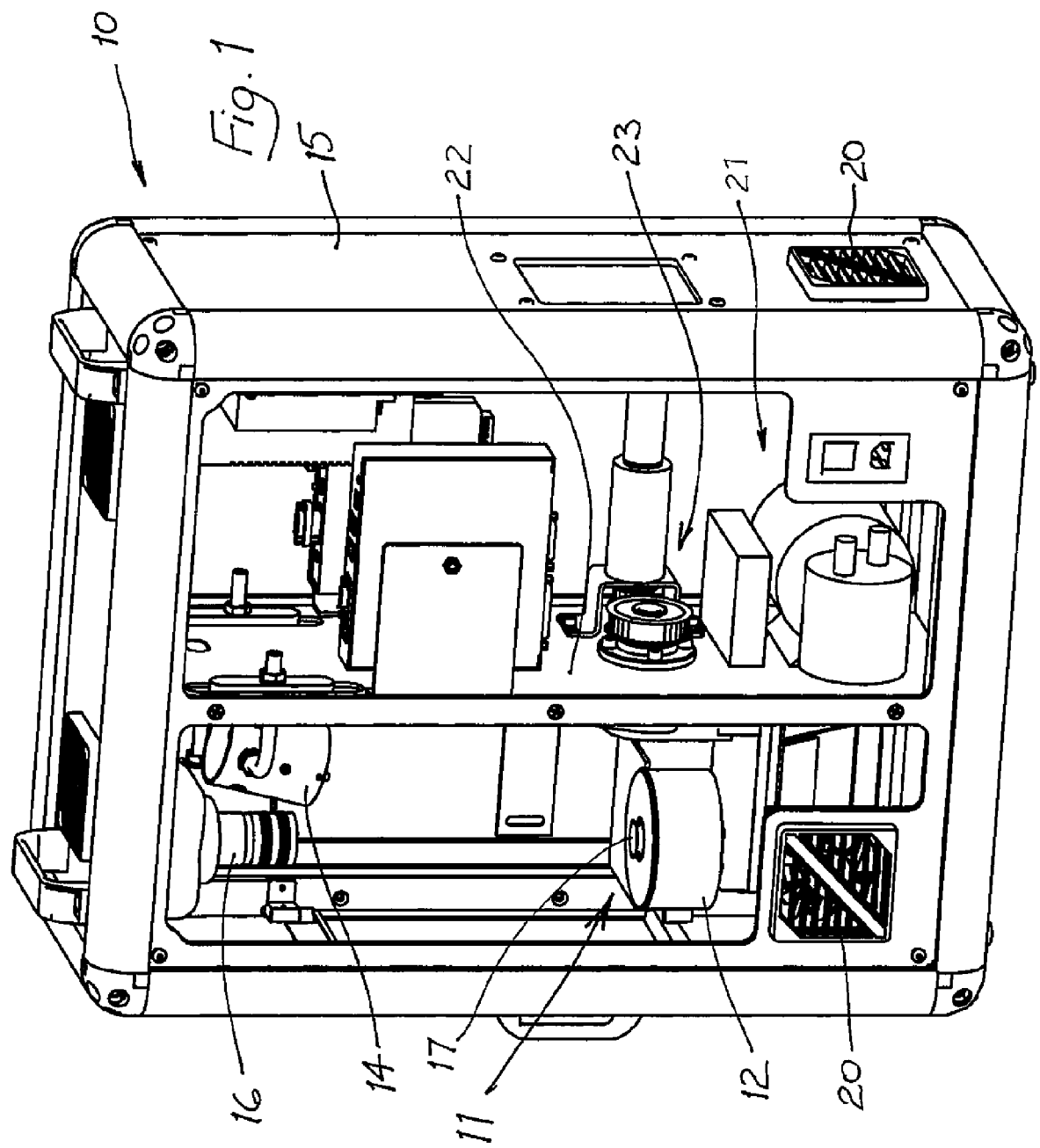
FIG. 1 is an isometric side view of a gemstone assessment, evaluation and grading apparatus according to a first embodiment of the invention.
Figure 2:
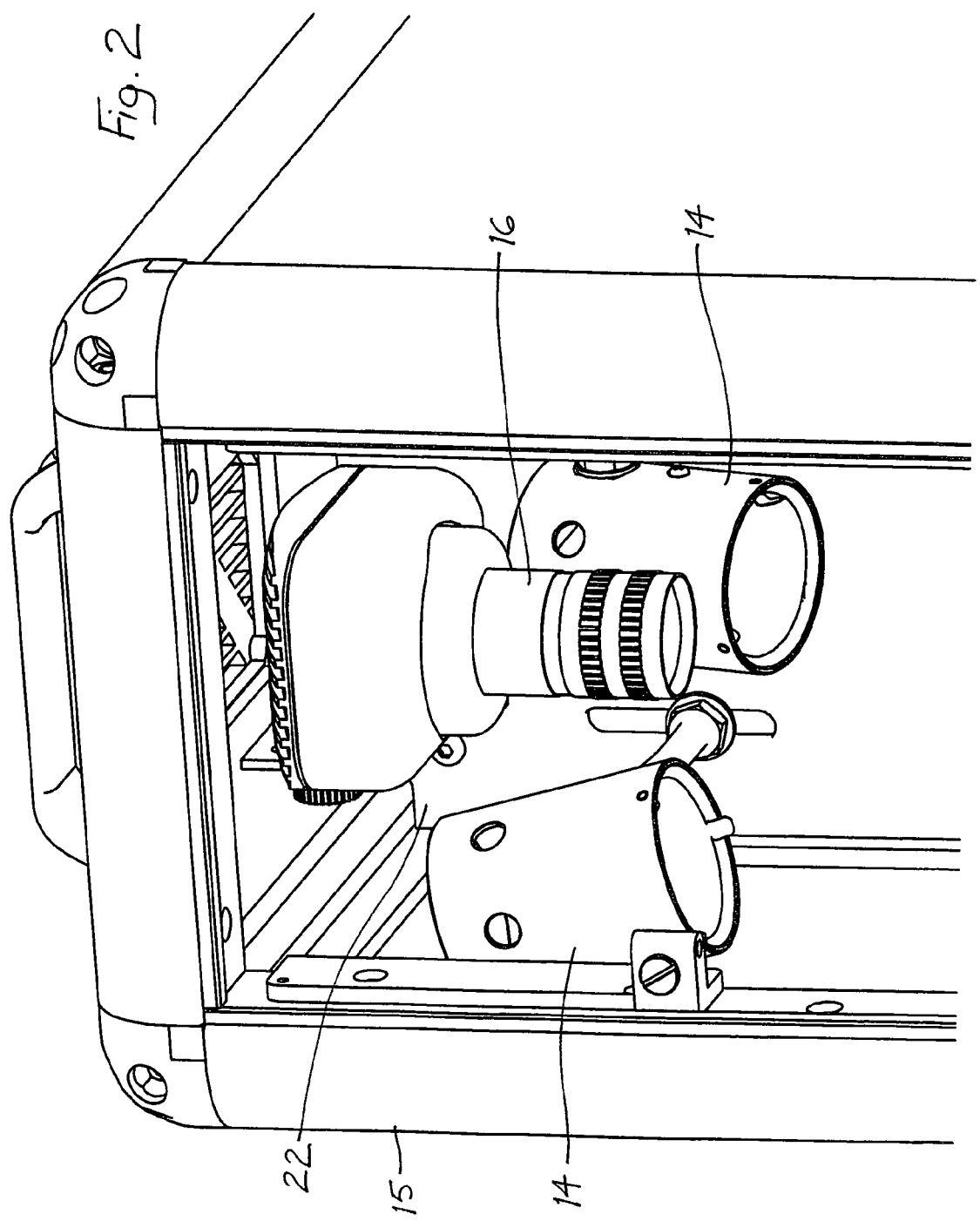
FIG. 2 is a view of the camera and lighting arrangements of the apparatus of FIG. 1.
Figure 3:
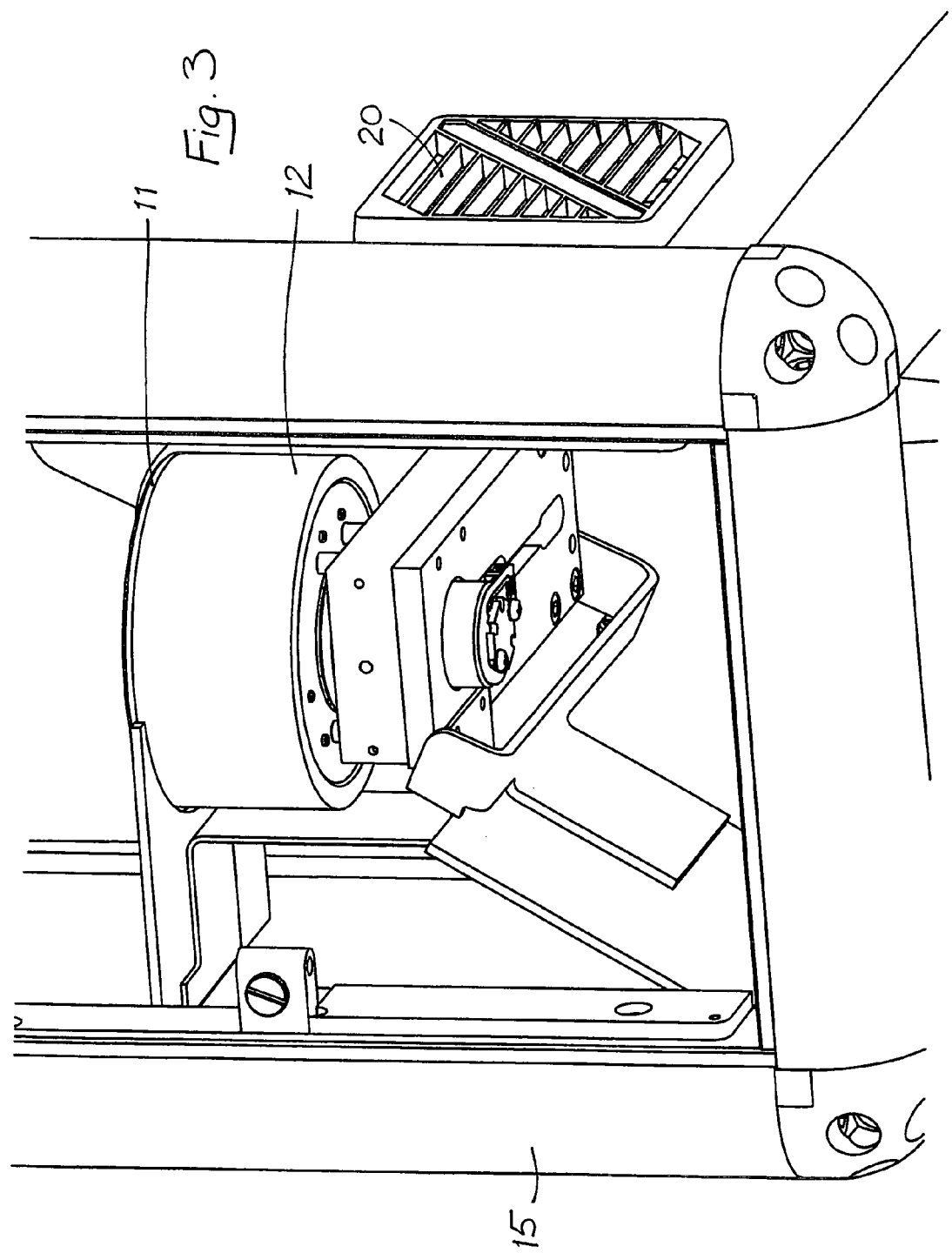
FIG. 3 is a view of the rotatable and tiltable stage arrangement of the apparatus of FIG. 1.
Figure 6:
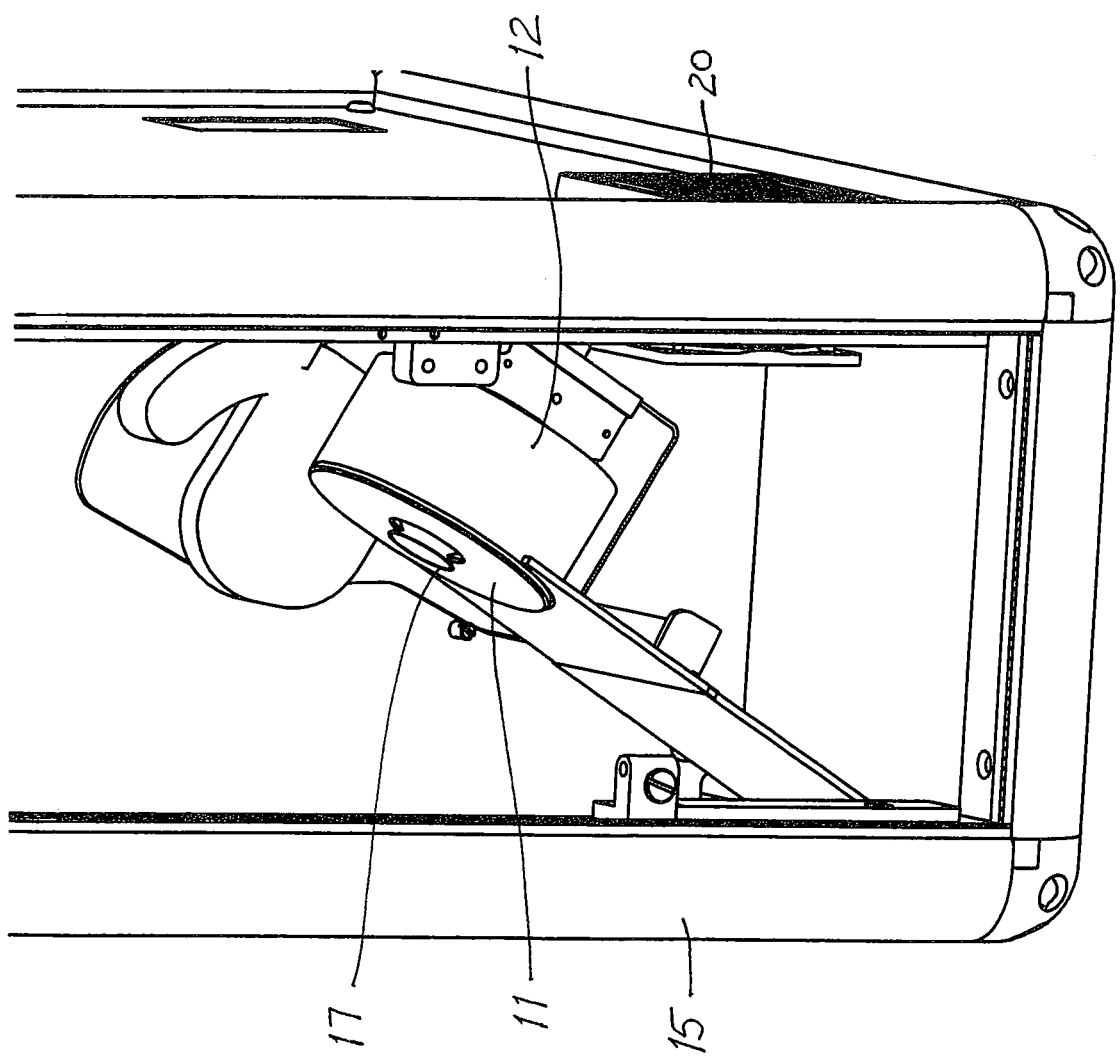
FIG. 6 is a view of the stage arrangement shown in FIG. 3 in a tilted position.

Referring to the apparatus 10 shown in FIG. 1, an opal is able to be placed on the stage 11 or platform of a goniometer 12, with the stage 11 being tiltable and rotatable by movement of the goniometer as shown in FIG. 6. The opal may have a maximum size of 5×5×2 cm for the stage 11. In this specification, the tilt and rotation angles will be referred to by the symbols φ and θ, respectively. A level or horizontal position of the stage corresponds to a reading of φ=90° when a camera 16 and one or more light sources 14 (see FIG. 2) are directly overhead. From the level position, tilting the stage 11 away from the one or more light sources 14 resulted in a reading decreasing from φ=90° to 0°.

Figure 4:
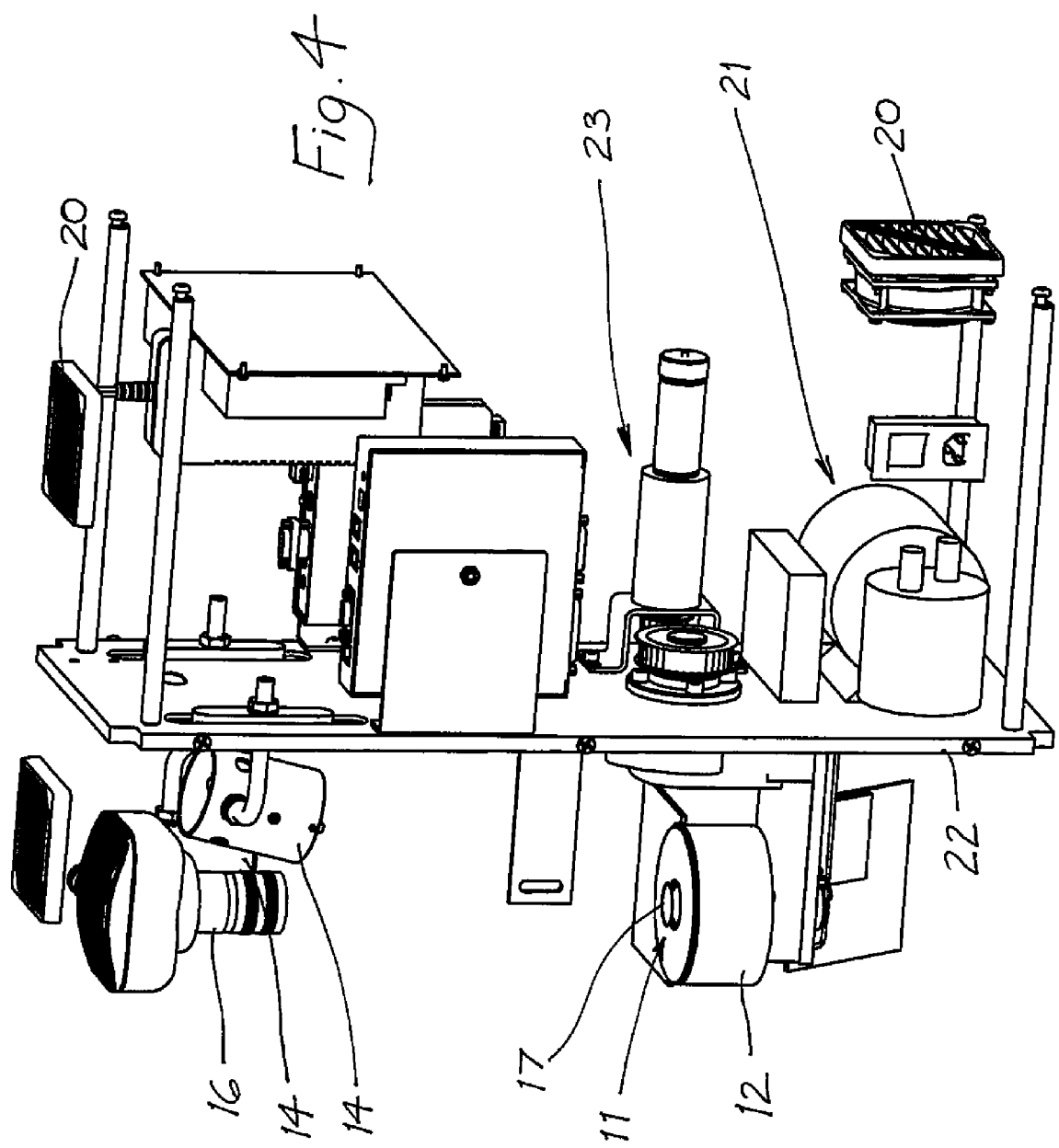
FIG. 4 is a view of the apparatus of FIG. 1 with its housing removed to show internal features.
Figure 5:
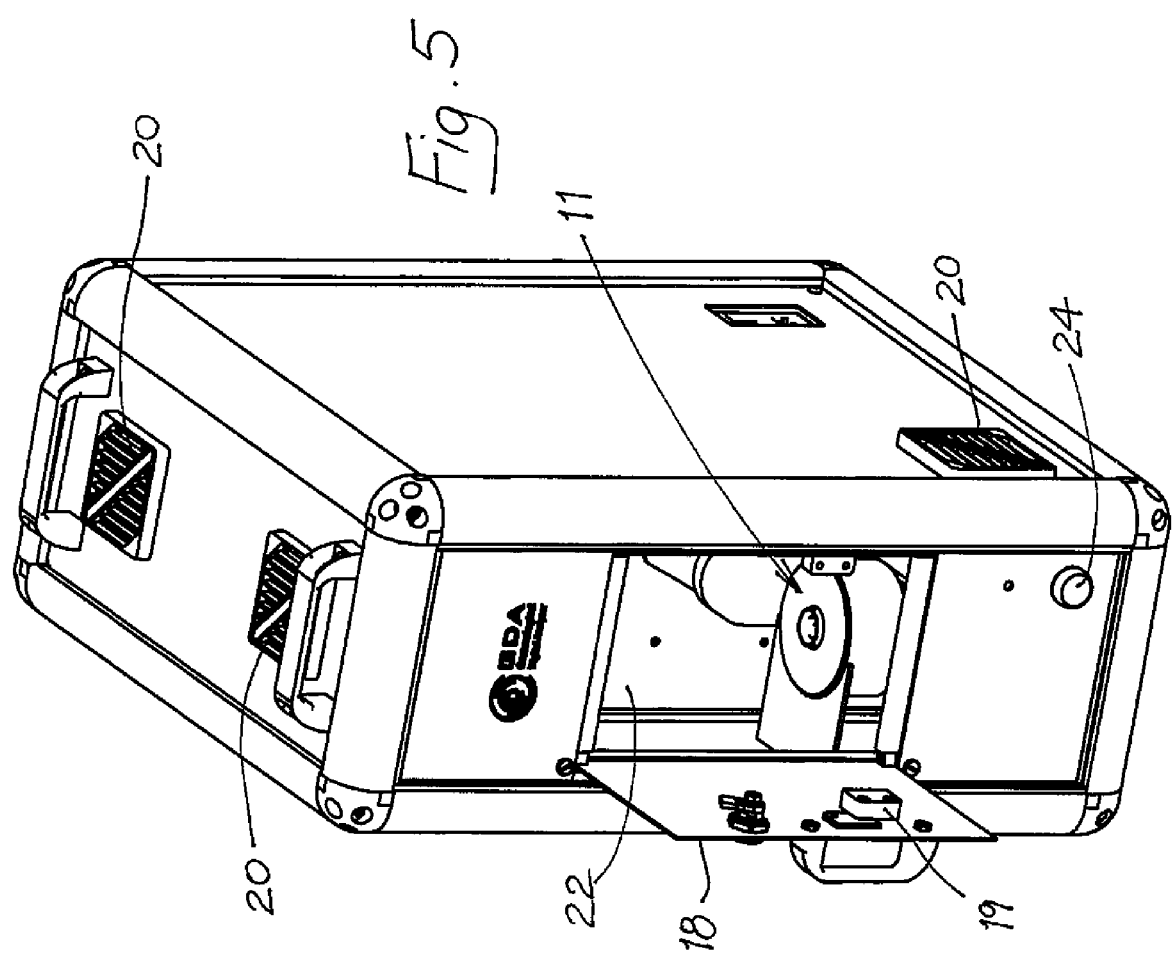
FIG. 5 is a isometric view of the apparatus of FIG. 1 with the door of the housing open.

The apparatus includes a light impervious housing 15, and the relative positions of the camera 16, the light sources 14 and the goniometer 12 within the housing are shown in FIG. 4. The position of the light sources 14, which are rotatably mounted, is alongside the camera 16, such that they are equidistant from the stage and the light sources 14 are as near co-incident as possible to the camera axis (i.e. over the shoulder). This is to replicate the lighting conditions used for human opal grading.

The housing 15 has an access door 18 for loading the opal onto the centre of the stage 11. The door 18 has a solenoid lock 19 so that it can be opened only when safe to do so, such as when the stage 11 has ceased any movement. When opened, the stage 11 will not be able to move.

Light proof cooling vents 20 are provided at the top and lower sides of the housing 15 to allow for convection cooling of the apparatus.

There is a motor control unit 21 located within a section of the housing 15 that is separated by a wall 22 from the camera 16, light sources 14 and the goniometer 12. The unit 21 has an on/off switch 24 and indicator lamp, and includes servomotor driver cards, contactors of lamps, safety circuitry and a main isolator connected to a personal computer (not shown) at which image calibration and image analysis will be controlled by software. A shaft and gearing assembly 23 driven by the motor control unit 21 controls the rotation and tilting of the goniometer 12 and its stage 11.

In order to quantify the colour characteristics of an opal, the two characteristics of flash or "play of colour" and body tone are critical.

The camera 16 captures a series of images at multiple angles in order to quantify the flash over the full range of viewing angles. Several image capture geometries are possible, such as tilting the rotation stage 11 holding the opal while keeping the camera and light sources fixed, or moving the camera and light sources while keeping the tilt angle of the rotation stage fixed, or some combination of these.

Initially the camera 16 is positioned directly above the rotation stage 11 containing the opal, wherein the stage is positioned at a tilt angle of 90°.

With back lighting, one image is captured to determine if the opal is translucent (i.e. crystal) and also to determine the region of interest (ROI) within the image that contains the opal.

With forward lighting, thirty-six images are captured at 10° intervals for 0° to 360° of rotation, although 5° intervals may be better suited to some opals. This series of images is repeated for 10° steps of tilt angle of the stage until a side view of the opal is achieved. Some opals may be better suited to 5° intervals of tilt angle. Although not shown, the camera 16, rather than the stage 11, may be adapted to tilt.

The opal is held tightly to the stage 11 by a flexible, silicon based suction cup 17 using suction from beneath the opal. By making the suction cup and the tubing from the suction cup to the vacuum pump of translucent material, this system does not occlude the opal in either forward or back lit views. It is capable of holding the opal firmly enough that the stage 11 can be tilted from 90° (overhead view) to 0° (side view) without the opal falling off. This means that a developer of the apparatus can choose the implementation which uses stage tilt rather than camera movement. This has the advantage of having a smaller footprint than the implementation that moves the camera.

Software is used to analyse these images to extract a summary of the flash and body tone characteristics and to display these measures in an easily comprehended manner. A description of each step in the software controlled analysis is provided later in the specification.

It will be apparent that the apparatus and methods described herein can be readily adapted for assessment, evaluation and grading of all coloured gemstones (including diamond, sapphire, ruby, and emerald).

Colour images were acquired using the camera 16 (Micropublisher RTV 5.0 manufactured by Qimaging). This camera has a dynamic range of 10 bits, corresponding to 1024 pixel intensity levels for each red, green and blue (RGB) channel (corresponding to a total of roughly one billion colours that the camera can discriminate). The number of pixels is 2560× 1920. The lens attached to the camera was a Randd Electronics macro lens. The focal length was 25 mm and the aperture was set to f/8.

As a light source 14, an incandescent light bulb was used. The glowing filament of an incandescent light bulb produces light with a broad spectrum. So, in terms of the breadth of its spectrum, it is more similar to daylight than other light sources, such as fluorescent tubes or light emitting diodes (LEDs) which have narrow spikes in their spectral distribution. The potential exists for the application of a light source in a "diffused" manner or oblique manner, so as to remove glint.

Seen from the position of the opal, the light bulb is a directional light source, covering an angle of approximately 9.1°. A disadvantage of directional illumination is that specular reflections from the surface of the opal, also called glints, can reflect the bright light of the light bulb directly into the camera. For surface positions where glints occur, the camera sensor is saturated and no information about the colour and brightness of the opal can be obtained. Therefore, areas of glint have to be detected in the images and excluded from further analysis, as described later in the specification.

A simple model for explaining the occurrence of flashes is to assume that facets within the opal act like small coloured mirrors. The viewer (or the camera) will therefore observe a flash when the angle of light incident on the opal is the same as the viewing angle. For a given light source, the observed area of flash will therefore depend on the solid angle covered by the light source. The smaller the solid angle (i.e. the more directional the light source), the smaller the area of flashes. For a large area light source, which is covering a large solid angle, flash will be observed over a larger area of the opal. Note that for the area of flash to become an objective criterion for assessing the quality of an opal, the directionality of the light source will have to be standardised.

For the image acquisition, each opal was placed on the suction cup 17 at the centre of the stage 11 of the goniometer 12 and secured with suction to prevent it from sliding off the stage at large tilt angles.

For all opals, the tilt angle $\phi$ was varied over a range of 90° in steps of 10°.

The rotation angle $\theta$ was also varied from 0° to 360° in steps of 10°.

As will be described in more detail later in the specification, the images taken at two different exposure times were combined into a single image with extended dynamic range. For this, the image taken at the long exposure time of 32 ms was used as a basis. Pixels that were fully saturated were replaced with the pixels from the image taken at 2 ms.

The extended range images obtained with the camera 16 are not suitable for calculating the colour and brightness values of the opals. First, lighting non-uniformities need to be corrected. Then, because each light source and camera has slightly different characteristics, the device-dependent RGB image needs to be calibrated to a device-independent measurement of colour. This measurement of colour needs to be appropriate for describing the colour characteristics of flash and body tone in terms that a person will understand.

Image Calibration

Extended Exposure

The brightness of opals covers a very wide dynamic range, from very dark areas of body tone to flash regions that are typically orders of magnitude brighter. This range of brightness exceeds the dynamic range that a standard camera can capture in a single image. To capture the full range of brightness encountered in opals without losing information due to over- or under-exposure, a pair of images is captured at different exposure times. The chosen camera has a 10-bit dynamic range for each red (R), green (G) and blue (B) channel image giving pixels in the range of 0 to 1023. Images $I_{short}$ and $I_{long}$ are captured at two exposures, 2 ms and 32 ms respectively, and combined to give an image of extended dynamic range, $I_{ext}$, as shown in Eqn 1 below. This gives a brightness range of 0 to >10,000.

$$I_{ext} = \begin{cases} I_{long} & \text{if } I_{long} < thr \\ I_{short} * \text{exposure.scaling} & \text{if } I_{long} >= thr \end{cases} \quad \text{Eqn 1}$$

where thr is 900 and the exposure.scaling is given by the ratio of the means of $I_{long}/I_{short}$ for a standard Kodak White card.

Figure 7:
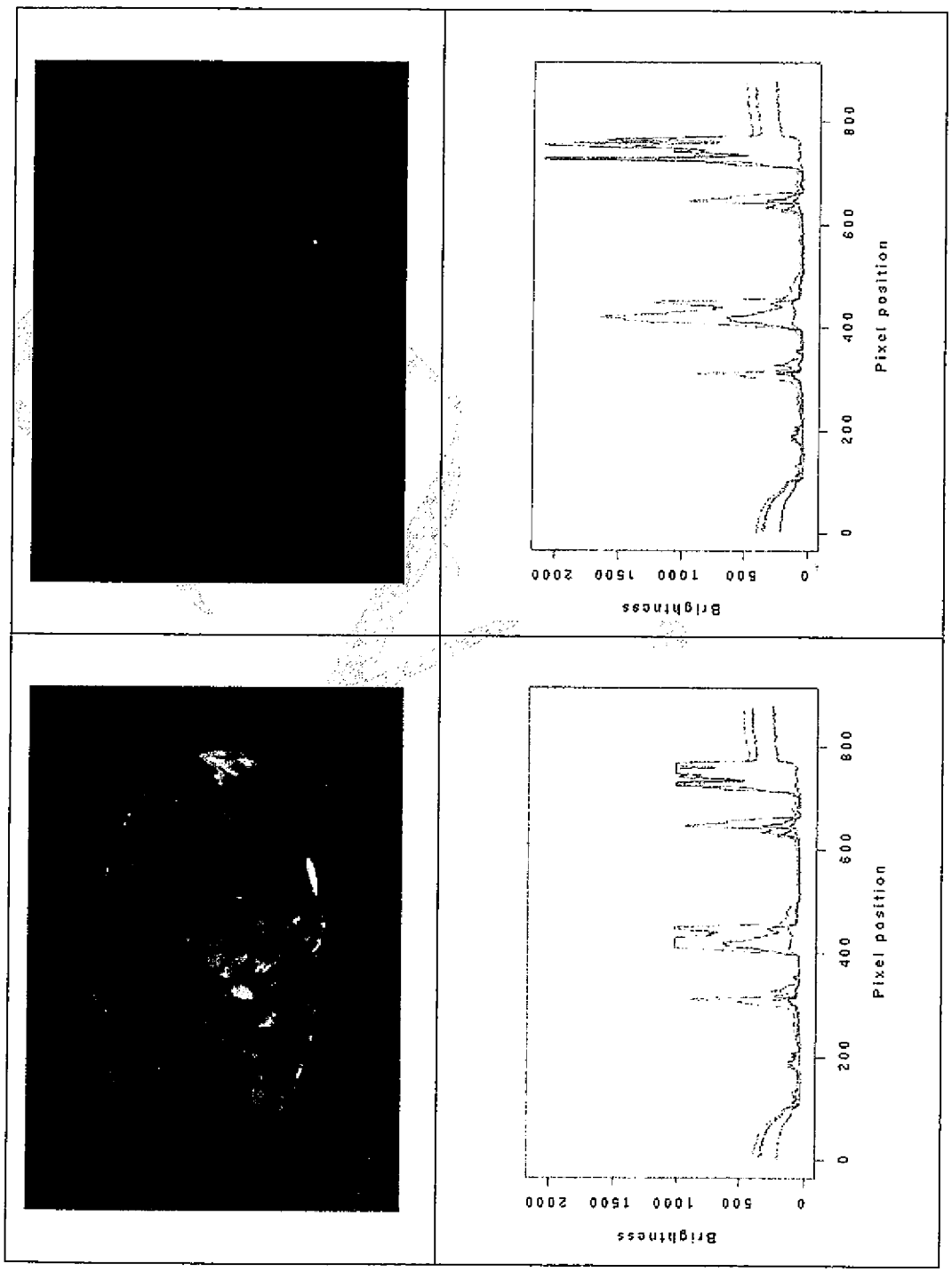
FIG. 7 provides a graphical comparison of long exposure image $I_{long}$ and extended exposure image $I_{ext}$ for a horizontal transect of an opal subject to image calibration.

An example is provided in FIG. 7 where there is shown, at left, $I_{long}$ with a horizontal transect taken through the centre of the image showing saturation of the brightest regions of flash (i.e. clipping of the G & R at 1023) and, at right, $I_{ext}$ with the horizontal transect showing that the extended dynamic range removes the saturation of the flash.

Lighting Correction

With a single light source, the lighting is often not uniform across the field of view of the camera. It will tend to be brighter in the centre of the lighting field. To correct for these lighting non-uniformities, two lighting field images are acquired, $I_{white}$ and $I_{grey}$, of standard Kodak White card and Kodak Grey card respectively. The Kodak White card has 90% reflectance across the visible spectrum and the Kodak Grey card has 18% reflectance. Assuming the CCD sensors in the camera are linear, these lighting field images can be used to correct the extended range image $I_{ext}$ consisting of channels $R_{ext}$, $G_{ext}$, and $B_{ext}$. The lighting corrected image $I_{cor}$ is derived as shown in Eqn 2 below.

$$L_{max} = \max(\text{mean}(R_{ext}), \text{mean}(G_{ext}), \text{mean}(B_{ext}))$$

$$I_{cor} = (I_{ext} - I_{grey}) * L_{max} * (90-18)/90/(I_{white} - I_{grey}) + L_{max} * 18/90 \qquad \text{Eqn 2}$$

where $L_{max}$ is the scalar maximum of the means of the channel images.

Colour Calibration

Because the CCD sensors in colour cameras can have different sensitivities and because the spectral characteristics of the light source can vary with time, the lighting corrected image, $I_{cor}$ is specific to the hardware set-up of the apparatus. In other words, it is a device-dependent, relative measure of colour. The process of converting the image to a device-independent, absolute measure of colour is called colour calibration.

Device-specific RGB to Device-independent XYZ

In order to convert from device-specific RGB values to device-independent XYZ values as defined by the CIE (Commission Internationale de I'Eclairage, or International Commission on Illumination), we need a calibrated colour checker card such as a Munsell or Macbeth card which has several colour swatches of known device-independent XYZ values. By capturing an image of this card and extracting the mean RGB values for each colour swatch, the transformation matrix, RGB2XYZ, can be determined by linear regression between the measured RGB values and the supplied XYZ values. Thus the RGB values in the $I_{cor}$ image can be converted to XYZ values in the $I_{XYZ}$ image using this matrix.

Device-independent XYZ to Gamma'd Device-independent sRGB

Although the device-independent XYZ measure of colour is an internationally recognised standard for colour representation, it is linear (unlike the human visual system) and not easily understood by non-experts, so it has been converted to a standard RGB representation, called sRGB. The D65 illuminant of this standard is designed to match noon daylight which is typical of home and office viewing conditions. The non-linear transfer function (gamma curve) closely matches that of the human visual system. If sRGB images of opals are viewed on sRGB calibrated monitors, they will closely match the actual opal appearance if viewed under natural daylight (D65 lighting conditions). So the $I_{XYZ}$ image is converted to the sRGB calibrated image, $I_{sRGB}$, using the standard transformation matrix, XYZ2sRGB, shown in Eqn 3 below.

$$XYZ2sRGB = \begin{array}{c} R \\ G \\ B \end{array} \begin{array}{ccc} X & Y & Z \\ 3.240479 & -1.537150 & -0.498535 \\ -0.969256 & 1.875992 & 0.041556 \\ 0.055648 & -0.204043 & 1.057311 \end{array} \qquad \text{Eqn 3}$$

Gamma'd sRGB to Non-linear Look-Up Table'd sRGBlut

Figure 8:
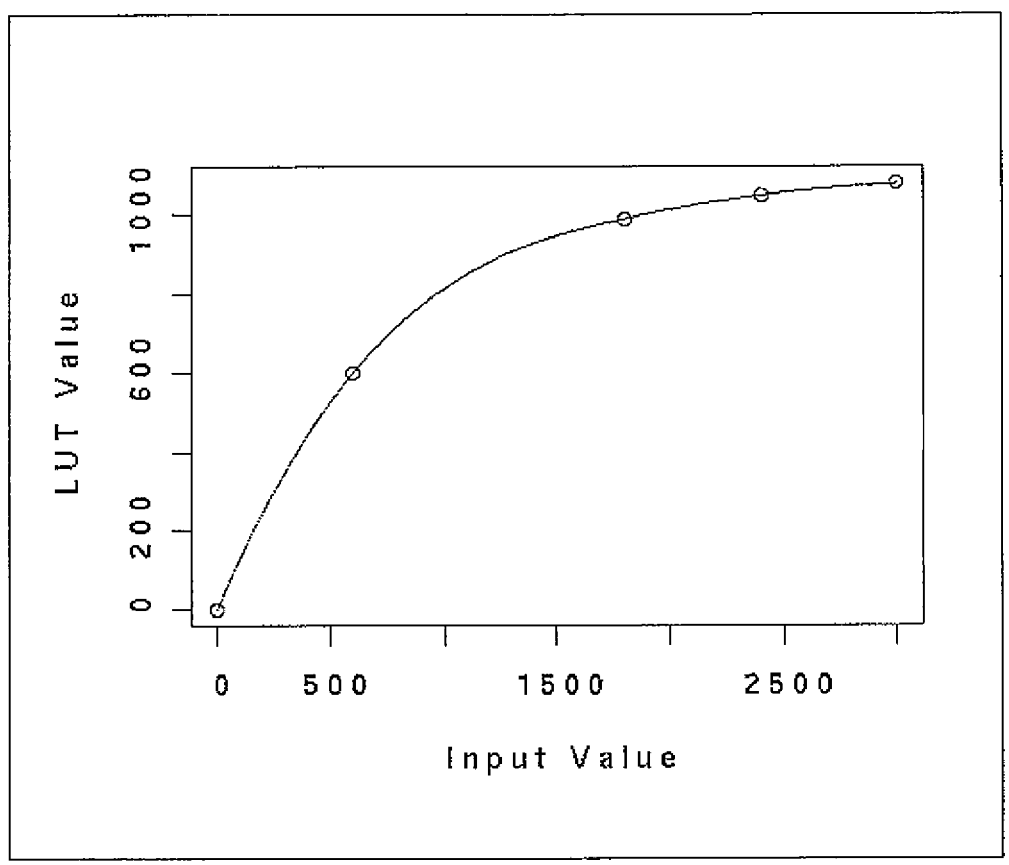
FIG. 8 is a line graph of input brightness values (x axis) against a Look-Up Table (LUT) transfer value of output brightness for an opal subject to image calibration.
Figure 9:
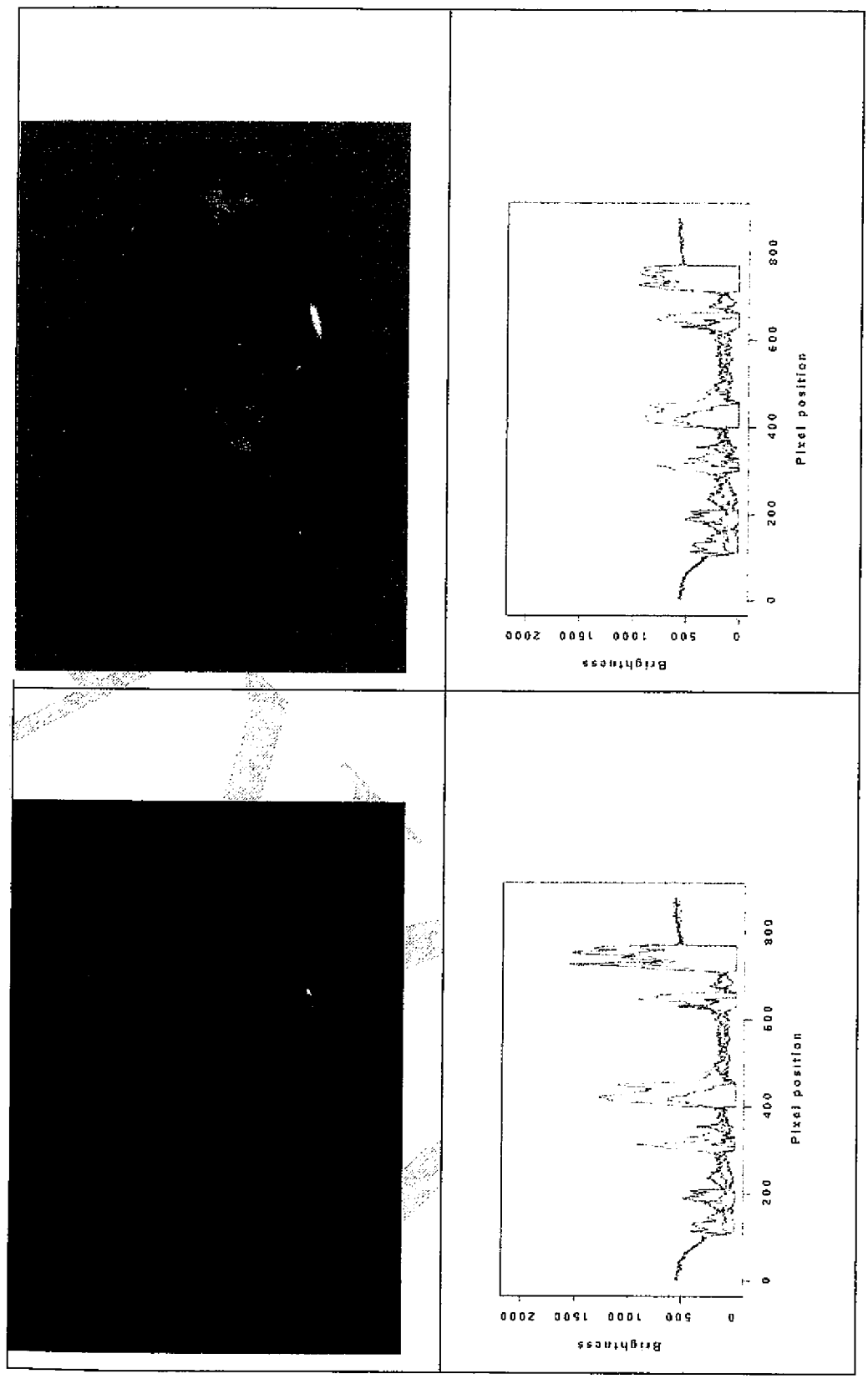
FIG. 9 provides a graphical comparison of standardised image $I_{sRGB}$ and LUT-compressed image $I_{sRGBlut}$ for a horizontal transect of an opal subject to image calibration.

The sRGB standard is designed for display of images of diffuse reflecting objects such as the body tone of the opal. Because the flash is specular reflection from the internal crystal structure of the opal, it can be orders of magnitude brighter. No single image display will be able to accurately represent the colour of both the body tone and the flash. For this reason, a Look-Up Table (LUT) has been used to compress the dynamic range of the flash so that a realistic view of the body tone can co-exist with an approximate representation of the flash. This LUT is designed to be linear in the brightness range of the body tone, 0-Bflash (where Bflash ~700) and to compress flash brightness >Bflash as shown in FIG. 8. Applying this LUT to IsRGB gives the image $I_{sRGBlut}$, as shown in FIG. 9, where there is shown, at left, $I_{sRGB}$ indicating the true colour of the bright flashes but the body tone is relatively dark and, at right, $I_{sRGBlut}$ giving a true representation of body tone colour but the bright orange flash regions appear more yellow because of saturation.

Colour Transformation from sRGB to sHSB

The RGB representation of colour is commonly used in image capture and display devices, but it is not designed for describing human perceptions of colour. For this, transformation to an alternative representation of colour called HSB (or HSV) is required. HSB stands for Hue, Saturation and Brightness (also known as Value). Hue is a measure of the wavelength of a colour and is given as an angle between 0 and 360°. Saturation is a measure of the purity of colour or the amount of white added. A pure colour will have 100% saturation. For decreasing values of saturation, the pure colour is increasingly diluted with white. The Brightness (or Value) is a measure of the intensity of the colour. The brightest colour will have 100% brightness. For decreasing values of brightness, the pure colour is increasingly diluted with black. In the extended exposure images provided herein, the brightest colour Bmax (100%) has been scaled to 3000.

Because HSB is a simple transformation of the RGB values in an image, it is defined relative to the standards of the RGB values. Transforming sRGB values will give standardised "sHSB" values, relative to the D65 white point. Applying the RGB2HSB transformation (defined in Eqn 4 below) to the $I_{sRGB}$ image, gives the image $I_{sHSB}$.

$$H = \begin{cases} 0 & \text{if max} = \text{min} \\ 60° \times (g-b)/(\text{max}-\text{min}) + 0° & \text{if max} = r \ \& \ g >= b \\ 60° \times (g-b)/(\text{max}-\text{min}) + 360° & \text{if max} = r \ \& \ g < b \\ 60° \times (b-r)/(\text{max}-\text{min}) + 120° & \text{if max} = g \\ 60° \times (r-g)/(\text{max}-\text{min}) + 240° & \text{if max} = b \end{cases} \qquad \text{Eqn 4}$$

$$S = \begin{cases} 0 & \text{if max} = 0 \\ 1 - \text{min}/\text{max} & \text{otherwise} \end{cases}$$

$$B = \text{max} * Bmax$$

where r, g, b are the R, G, and B values, respectively, of a pixel scaled to the range from 0-1; max is the maximum of r, g, and b, and min is the minimum.

Image Analysis by Segmentation and Histogram Measurement

Having colour calibrated all the images captured at the multiple viewing angles, it is necessary to identify the portion of each image containing specific regions of interest, such as the stone or glint. This process is called segmentation.

Segmentation

Stone Segmentation in Back Lit Images

Figure 10:
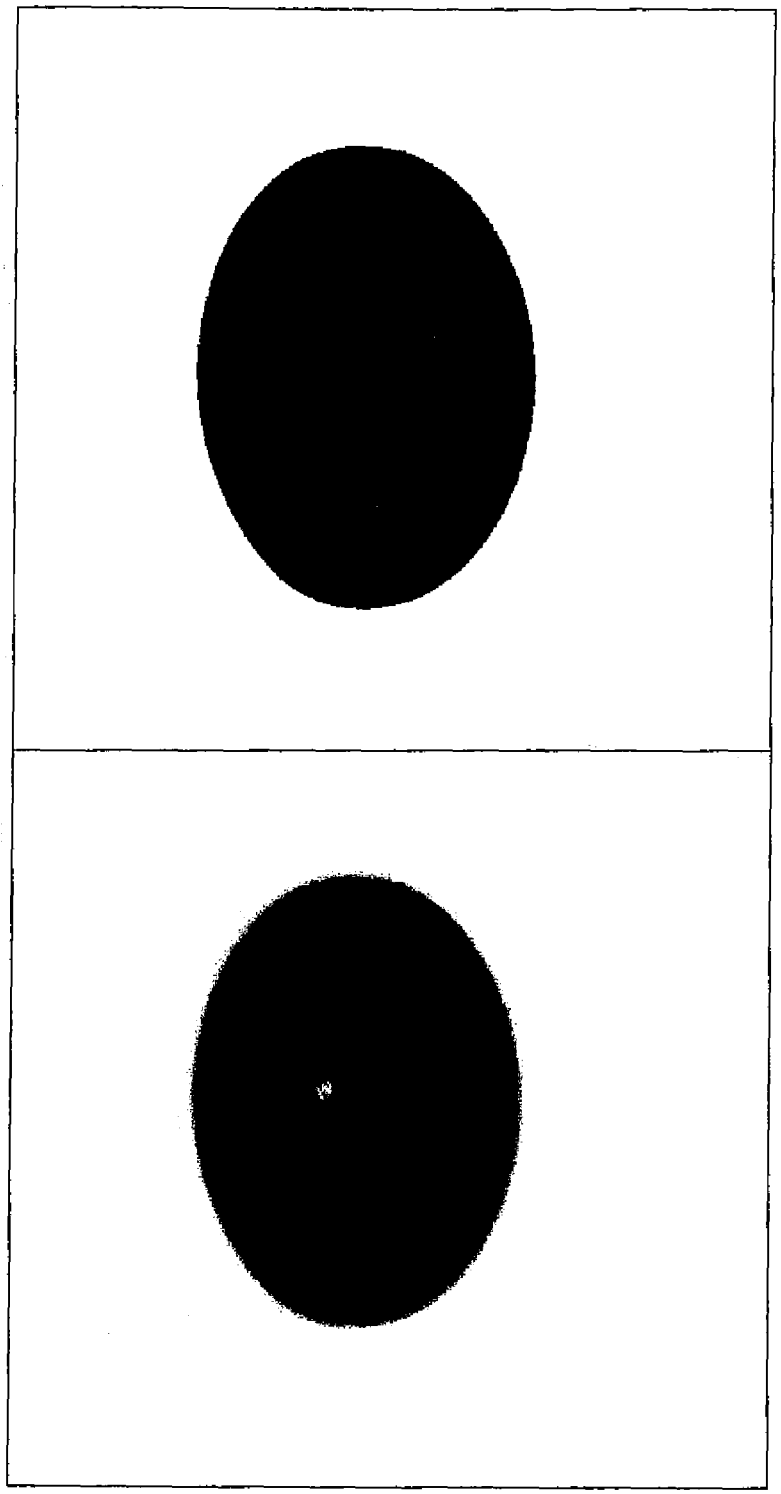
FIG. 10 shows the segmentation of a back lit image of a stone (at left) and a stone mask (at right).

In order to reduce the amount of time taken to capture the multiple images with forward lighting, it is useful to locate the region of interest, ROI, within the image that contains the opal. This is most easily derived from a back lit image rather than a forward lit image because the back lit image has greater contrast between the background and the stone. Therefore the first image to be captured is a back lit view with the stage tilt angle at 90°. This is easily segmented by simple thresholding of the average brightness of the three channels as shown in FIG. 10. The ROI so derived can be used to restrict the area of the image to be captured and processed for all the forward lit images. This can greatly reduce the time to measure each opal.

In the case of translucent, crystal opals, an additional threshold is used to locate any opaque veins of potch running through the crystal. A mask of these opaque regions is required later when determining the body tone of the stone.

Stone Segmentation of Forward Fit Images

Unlike the back lit image, segmenting the forward lit images is a much more challenging task for several reasons. The opal can be both brighter than the background (in the case of white opals) and darker than the background (in the case of black opals). Also, depending on the angle of tilt of the stage, the brightness of the background varies in intensity from nearly white (when viewed from the top) to nearly black (in the side-on view). So a simple threshold cannot be used to separate the opal from the background. In addition, shadows at the edge of the opal mean that simple measures of the uniformity of colour and brightness of the background cannot be used to segment the opal.

Figure 11:
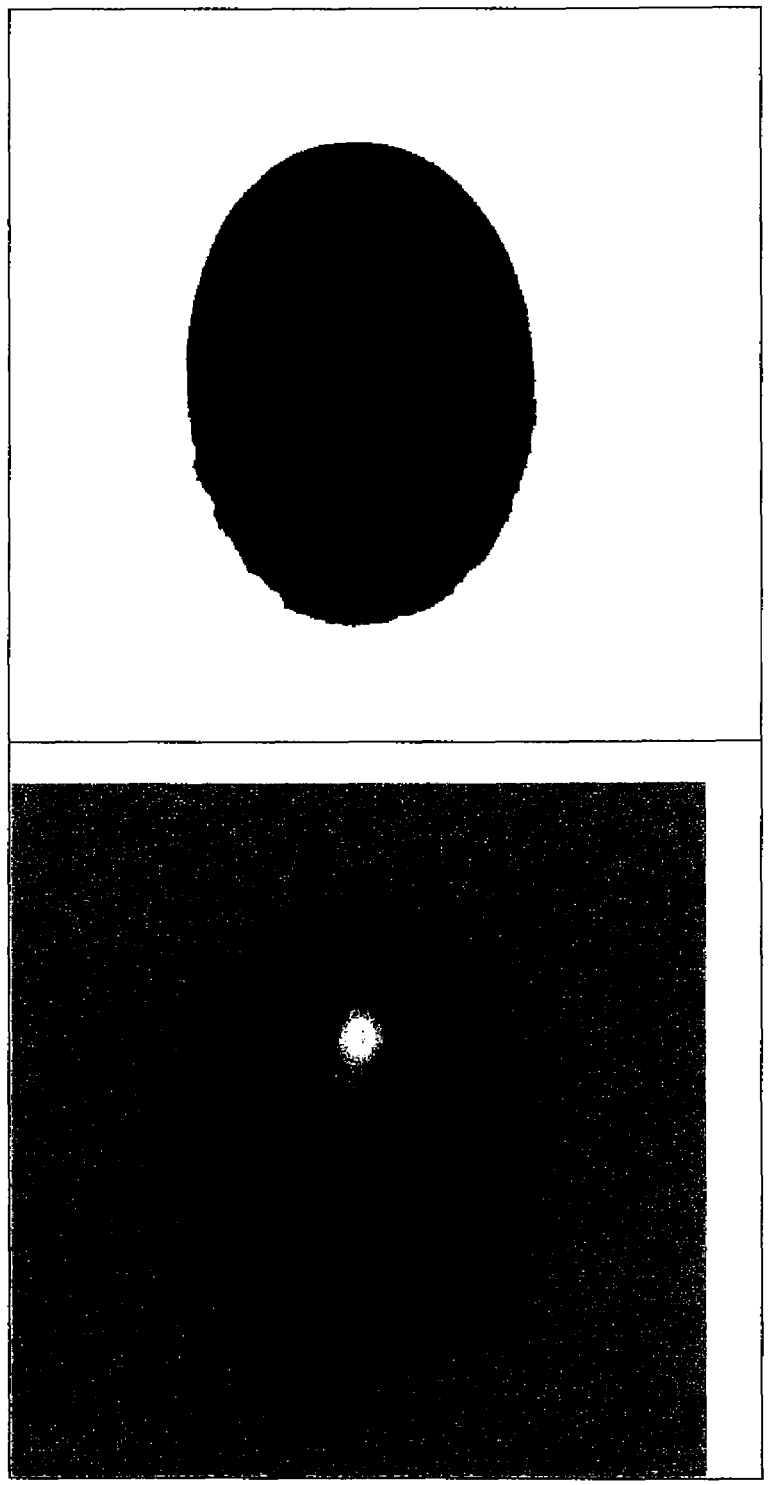
FIG. 11 shows the segmentation of a forward lit LUT-compressed $I_{sRGBlut}$ image of a stone, with the forward lit image of the stone (at left) and a stone mask (at right).

The segmentation is performed on the LUT-compressed $I_{sRGBlut}$ image (see FIG. 11) since it gives more weight to the part of the dynamic range containing the transition between background and stone. The segmentation algorithm is a sequence of operations, roughly as follows: transform the image into a form that enhances non-uniformities such as the edges of the opal, colour texture and the edges of flash (the transform used is the maximum of the local pixel-wise variance of the R, G and B channels); threshold this image to get seeds within the opal (high variance); generate background seeds that are an empirically determined distance from the opal seeds; and find the watershed boundary between the two sets of seeds in the gradient of the variance image.

Glint Segmentation of Forward Lit Images

Figure 12:
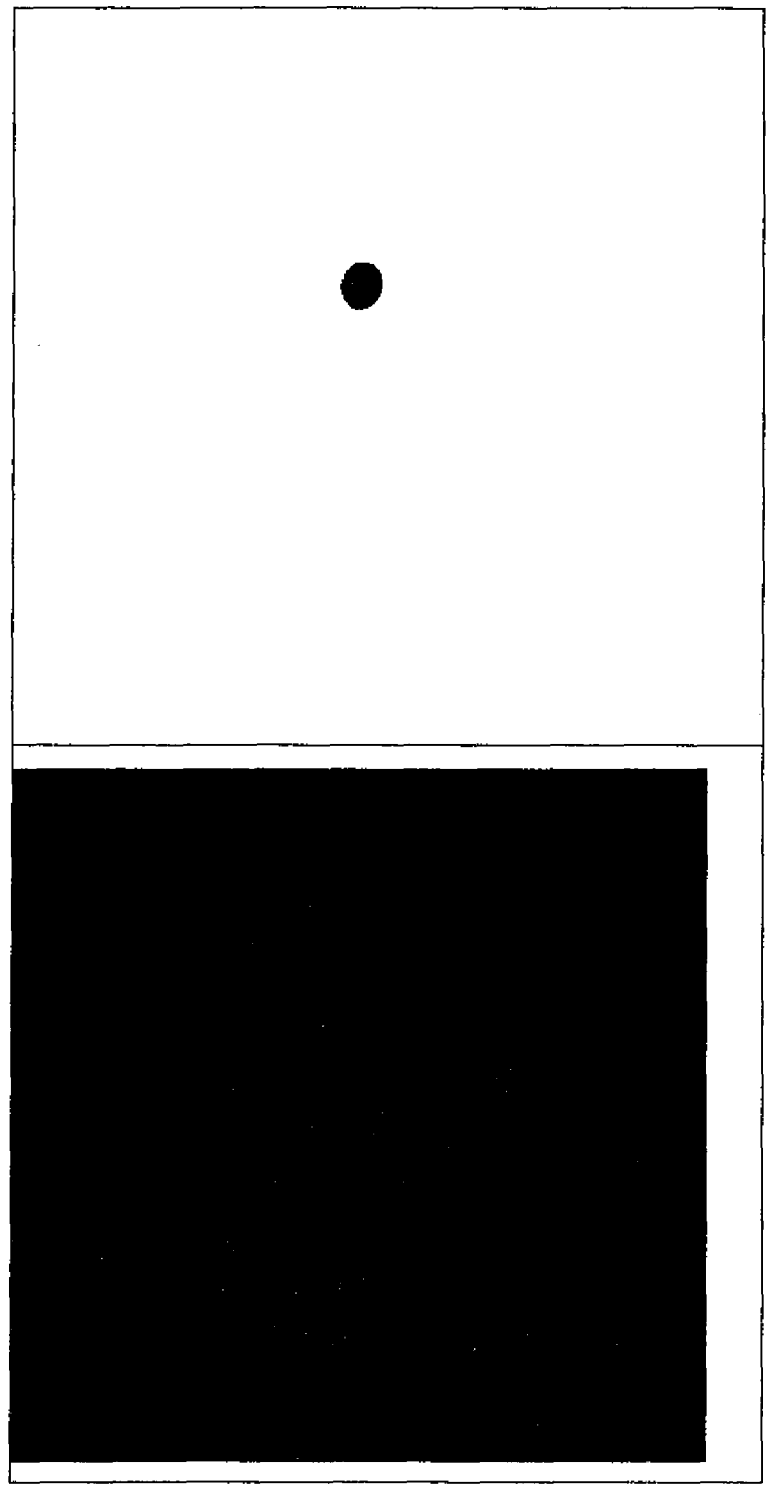
FIG. 12 shows the segmentation of glint in the sHSB image $I_{sHSB}$, with the forward lit sHSB image (at left) and a glint mask (at right).

Having defined the mask of the opal, the portion of the opal containing glint needs to be excluded. This is easily segmented by using the fact that glint is both bright (high Brightness or Value) and white (low Saturation). It is simplest to take the logical AND of the results of thresholding S<Sglint (40%) and B>Bglint (1200) of the $I_{sHSB}$ image (see FIG. 12).

Body Tone Segmentation of Forward Lit Images

As described above, the mask or ROI of the image containing only the opal has been determined by excluding the glint regions and, in the case of crystal opals, by excluding the internal opaque regions since these will interfere with the measurement of the body tone of the crystal. Now the regions which display body tone need to be determined before the colour characteristics of that body tone can be measured. If the stone only has opal in its face, then the body tone regions will be those where the flash is "turned off", in other words, where it is not visible from that viewing angle. These regions will be the darkest part of the stone. However, this simple definition of body tone region is not valid in all cases. If the stone has either potch (opal without the crystal structure which causes flash) or boulder (the rock in which the opal is embedded) present in the face, then the darkest part of the stone may well belong to these "non-opal" regions rather than to the body tone of the opal present in the face.

To distinguish between opal and "non-opal" regions of the stone, use is made of the fact that "non-opal" regions remain the same when viewed from different angles. Geometric distortion of the stone will be present if a comparison is made of images from a stage tilt angle other than 90°. This means that a comparison must be made of images taken at different stage rotation angles (or different lighting angles) for a 90° stage tilt angle. Images taken at different stage rotation angles must be rotated back in software in order to align them before they can be compared. This step is not necessary if different lighting angles are used. If different lighting angles are used, then each separate light source must have its own set of colour calibration files. The "non-opal" regions are those which do not change their appearance in these multiple view images.

Flash Histogram Measurement

Unlike body tone which is view-angle independent, the flash in an opal changes from each viewing angle. In the hardware set-up of the apparatus, it has been established that a sampling frequency of 10° is necessary in both rotation and tilt angles to ensure that no flash regions are missed. This requires the capture and analysis of 324 images to cover the full range of viewing angles. This is challenging to measure and even more so to display in a way which conveys a summary of these measurements.

3D Histogram of Stone HSB Values

For each image, a stone mask has been identified which excludes the background and glint regions. No attempt has been made to exclude "non-opal" regions or body tone regions because these are only established at one tilt angle. A summary of the stone colour characteristics is created by taking a histogram of sHSB values present within the mask. Each histogram is a 3D array of the counts of pixels falling within bins of Hue, Saturation and Brightness value. There are 30 Hue bins linearly spaced in the range of 0 to 360°. Saturation has 10 bins between 0 and 100%. Brightness has 20 bins piece-wise linearly spaced to give 10-15 bins in the range containing body tone (0-Bflash) and 5-10 bins in the range containing flash (Bflash-Bmax).

If the pixel count in each bin is divided by the number of pixels in the stone (including glint regions), then the bin value gives the proportion of the stone having the HSB values of that bin.

This is a very compact summary of the colour information. For example, the opal image may be 800×800 pixels. This requires 640,000 HSB values to store and display the colour information. By discarding the spatial context, the 3D histogram requires only 6,000 bins (30 H bins×10 S bins×20 B bins) to store this information. Also, because the spatial context has been discarded, histograms from multiple views can be added to get the average proportions of the stone having specific HSB values.

Figure 15A:
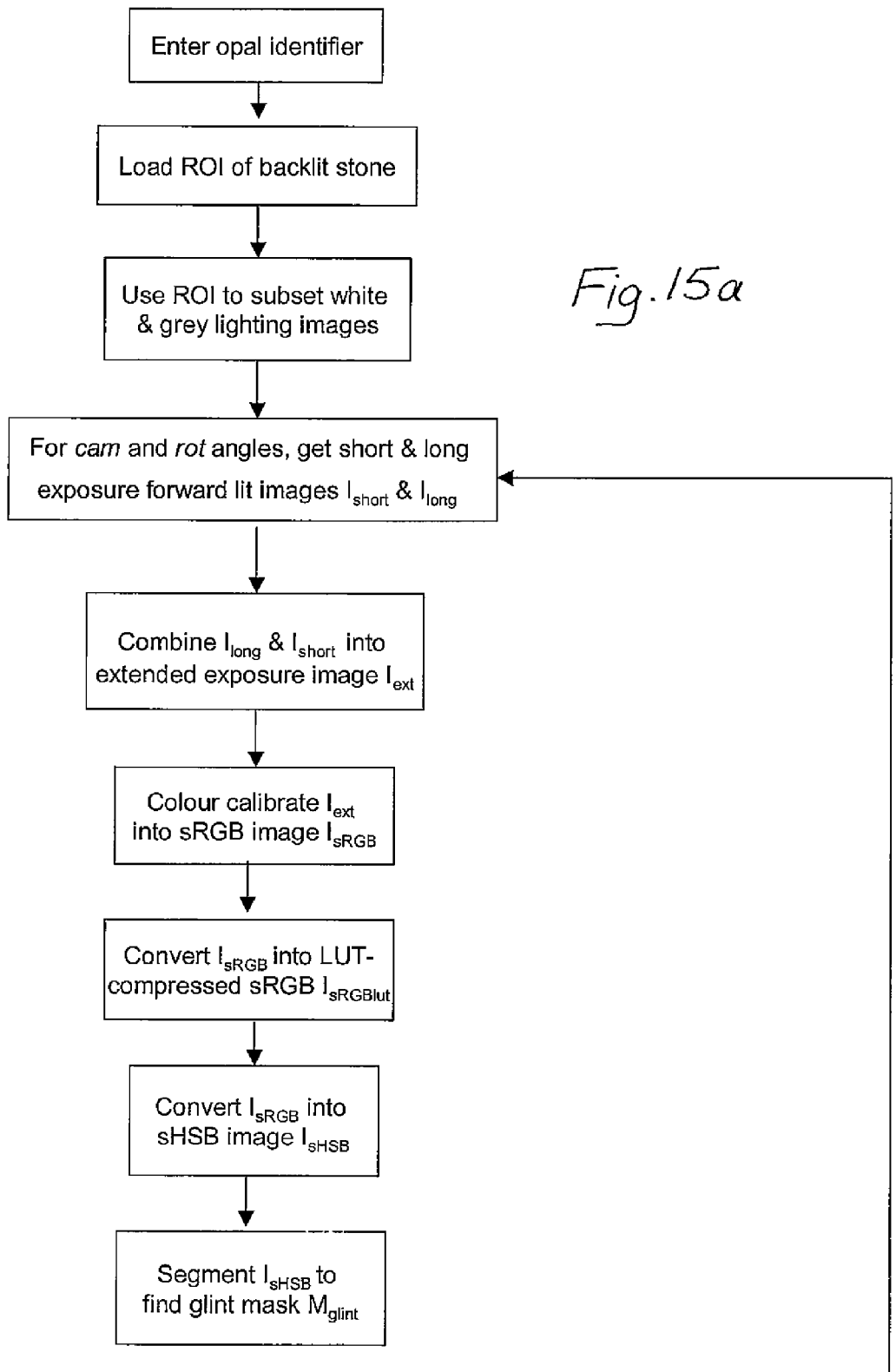
FIG. 15a is a logical flow diagram of a preferred software controlled, image calibration and analysis method for assessment, evaluation and grading of opals according to the characteristic of flash.
Figure 15B:
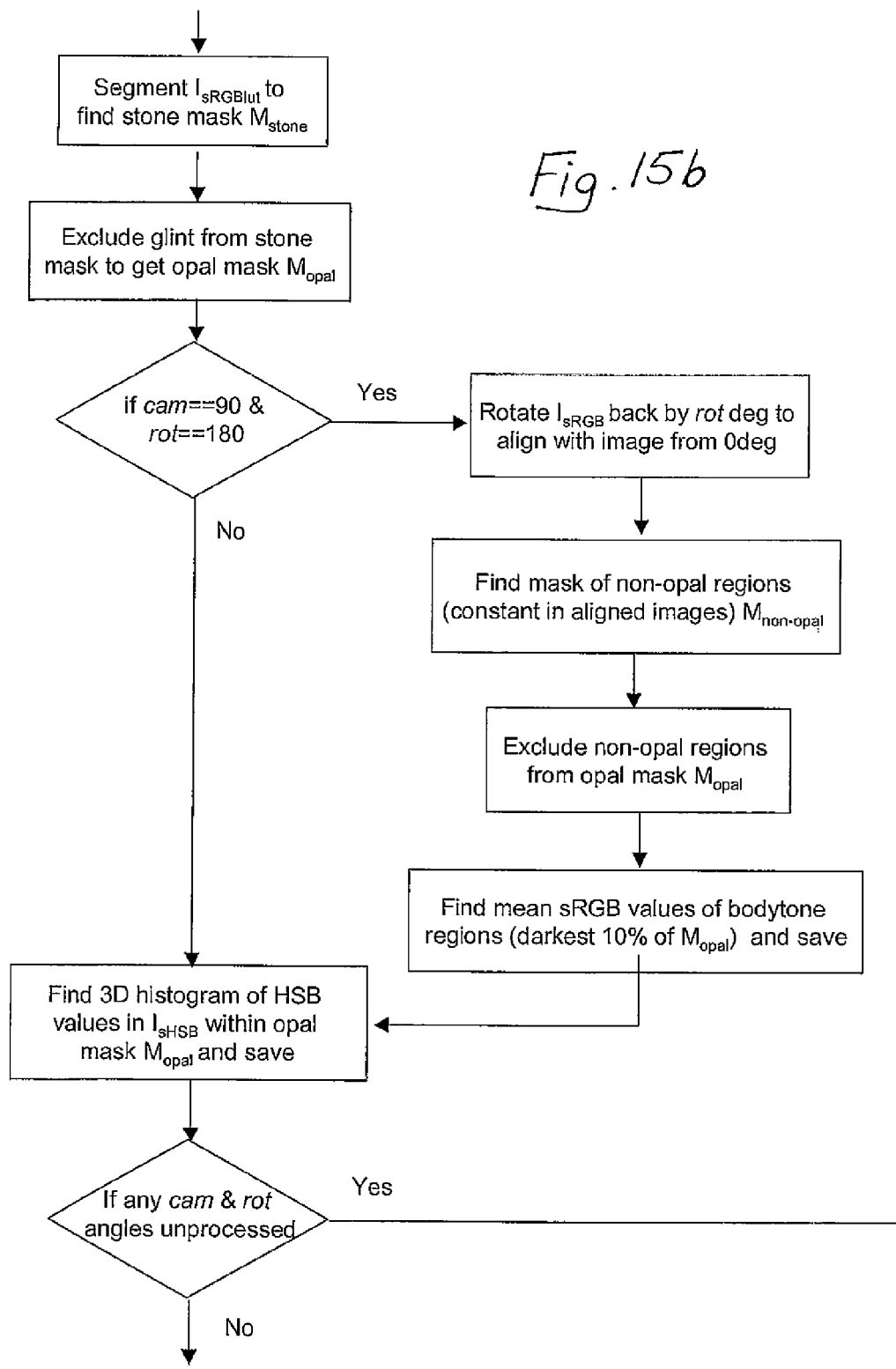

The summary 3D stone histogram (also referred to as a total 3D histogram, see FIG. 15) contains bin counts for both flash and body tone regions of the stone. These can be separated out by using the knowledge that flash is both bright B>Bflash (700) and quite highly saturated S>Sflash (50%). (Note that these flash Brightness and Saturation thresholds may be lowered if the Saturation values of the body tone and "non-opal" regions are known). The result is a 3D histogram of flash HSB values.

Summary Histograms of Flash H & B and H & S Values

The 3D flash histogram can be stored but it is difficult to display for easy human interpretation. Consequently, all the Saturation bins are first combined and a 2D summary histogram of Hue and Brightness values is created (a "Summary H&B Histogram"). Also, all the Brightness bins are combined and a 2D summary histogram of Hue and Saturation values is created (a "Summary H&S Histogram").

Summary H&B Histograms and H&S Histograms for two opals, "Golden Grace" and "Flatspot", are shown in FIG. 13.

The H&B Histogram is to be interpreted as follows: Hue is plotted on the x-axis; the height of each histogram bar is the area proportion of that Hue; within each bar, gradations of brightness are used to display the proportions of the area belonging to the various Brightness bins for that Hue. Similarly, the H&S Histogram is to be interpreted as follows: Hue is plotted on the x-axis; the height of each histogram bar is the area proportion of that Hue; within each bar, gradations of saturation are used to display the proportions of the area belonging to the various Saturation bins for that Hue. Note that these gradations are not as informative because flash does not tend to vary in saturation very much.

Note that according to the Summary H&B Histograms in FIG. 13, the maximum area proportion of a single Hue in "Golden Grace" is only about twice that of "Flatspot". However, when the images taken at 80 degree tilt angle are examined, it is obvious where the "Flatspot" stone gets its name. There is a flat spot in its flash when viewed from above. This information is not at all evident in the Summary Histogram. For this reason, 9 additional H&B Histograms were produced to summarise this directional information.

Directional Histograms of Flash H & B Values

Figure 14:
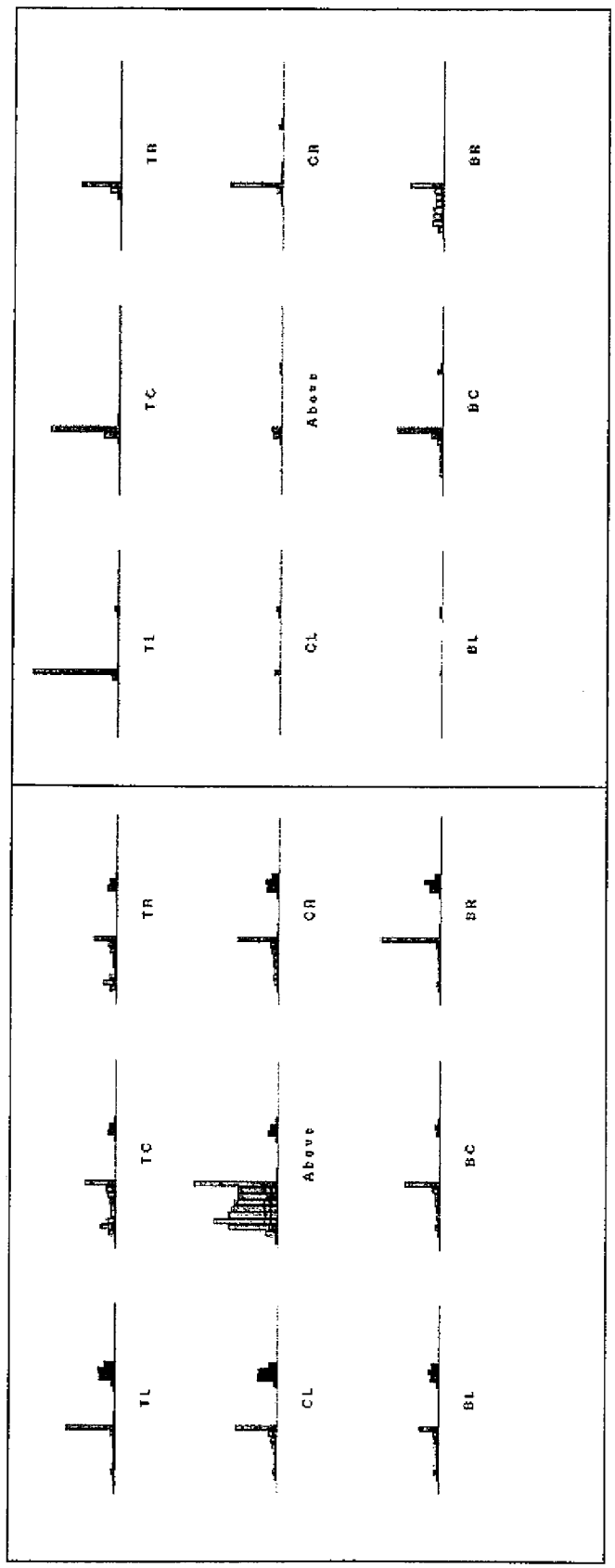
FIG. 14 provides a comparison of Directional Hue and Brightness Histograms of the two opals used in FIG. 13.

The Directional H&B Histograms for "Golden Grace" and "Flatspot" are shown in FIG. 14. Table 1 below defines the range of viewing angles that have been combined for each of the histograms.

The directional histogram for "Flatspot" clearly shows that there is very little flash when viewed from above but it flashes green strongly from the Top Left (TL) direction. By contrast, the directional histogram for "Golden Grace" shows that it displays the largest area of flash and is also most colourful (flashing orange, yellow and green) when viewed from above. This directional information will be important for buyers when choosing an opal for a setting which has specific directionality constraints, such as a pendant or brooch, rather than for a ring which can be easily viewed from many directions.

TABLE 1

Definition of viewing angle ranges for directional histograms where tilt is the stage tilt angle and rot is the stage rotation angle.

| | |
|---|---|
| Above | (tilt > 60°) |
| BC—bottom centre | (tilt <= 60°) & ((rot > 337.5°) \|\| (rot <= 22.5°)) |
| BR—bottom right | (tilt <= 60°) & ((rot > 22.5°) & (rot <= 67.5°)) |
| CR—centre right | (tilt <= 60°) & ((rot > 67.5°) & (rot <= 112.5°)) |
| TR—top right | (tilt <= 60°) & ((rot > 112.5°) & (rot <= 157.5°)) |
| TC—top centre | (tilt <= 60°) & ((rot > 157.5°) & (rot <= 202.5°)) |
| TL—top left | (tilt <= 60°) & ((rot > 202.5°) & (rot <= 247.5°)) |
| CL—centre left | (tilt <= 60°) & ((rot > 247.5°) & (rot <= 292.5°)) |
| BL—bottom left | (tilt <= 60°) & ((rot > 292.5°) & (rot <= 337.5°)) |

The software controlled, image calibration and image analysis method described above is summarised in FIGS. 15a to 15c. The image calibration involves the steps of (i) subjecting an opal to extended exposure, (ii) lighting correction, (iii) colour calibration and (iv) colour transformation from sRGB to sHSB. The image analysis involves then subjecting a so calibrated image to (v) segmentation and (vi) histogram measurement, in order to provide an objective assessment of the flash characteristic of the opal. The image analysis may be extended to include body tone measurement.

Body Tone Measurement

In order to measure body tone, 3D histogram bins for the full range of Hue, Saturation and Brightness values within a stone that were created in a manner as described earlier in the specification, and the method for finding the body tone region in an image that was described earlier in the specification, are taken in consideration by the software to calculate the mean or average sRGB values within this region, convert to HSB values and assign to one of the 3D histogram bins. The H, S and B value of the body tone can then be reported.

In summary, it may be appreciated from the above description of preferred embodiments of the invention that:—

High dynamic range imaging (exposure blending) is required to cover the full range of brightnesses between different opals, The different brightnesses of an opal can be objectively assessed using a digital camera, Under controlled lighting conditions and using proper calibration techniques, the range of colours can be objectively measured by specifying the hue, saturation and brightness values of each colour, As a means of reducing the large amount of data contained in the images, several binning and visualisation methods can be pursued, Body tone can be determined, and, The apparatus can be further used to assess, grade and evaluate all gemstones, including inorganic gemstones and minerals, such as, or other than, opals.

It will be apparent to persons skilled in the art that various modifications may be made in details of design and construction of the apparatus, and in method steps of the methods described above without departing from the scope of ambit of the invention.

For example, a useful image capture methodology is to secure the gemstone on a stationary stage (so as to eliminate any potential movement problems of the gemstone), and systematically move the at least one light source and camera to enable image capture sequences to simulate the required pitch, roll and yaw movements.

Furthermore, the apparatus may include a plurality of digital cameras and positioned lights, and all of the cameras may take images of the gemstone simultaneously, or in sequence, at predetermined angular increments during rotation of the stage.

The invention claimed is:

1. An apparatus for assessment, evaluation and grading of gemstones, comprising a stage upon which a gemstone may be supported, the stage being enclosed in a housing that is impervious to light, at least one light source located in the housing and adapted to project incident light onto the gemstone, means for rotating and tilting the stage so as to vary the orientation of the gemstone to the incident light, a digital camera located in the housing adjacent the or each light source and adapted to take images of the gemstone based on reflection and/or refraction of the incident light, and information processing means for calibrating and analysing the images, wherein the information processing means is programmed with an instruction set for colour calibrating the images and then analysing the colour calibrated images by segmentation and histogram measurement.

2. The apparatus of claim 1 wherein the stage is rotatable around 360° and tiltable around 90° by movement of a goniometer.

3. The apparatus of claim 1 wherein the stage includes a suction cup for holding the gemstone tightly using suction from beneath the gemstone.

4. The apparatus of claim 1 wherein the information processing means is programmed with a further instruction set for controlling the camera to capture a series of images at 10° angles for 0° to 360° of rotation and at 10° angles for 90° to 0° of tilt.

5. The apparatus of claim 1 wherein the instruction set is software programmed into a personal computer.

6. The apparatus of claim 1 wherein the gemstone is an opal, and the image colour calibration and image analysis is for assessing the characteristics of flash and body tone of the opal.

* * * * *